United States Patent [19]
Piché

[11] Patent Number: 4,677,842
[45] Date of Patent: Jul. 7, 1987

[54] ULTRASONIC DENSITY MEASUREMENT

[75] Inventor: Luc Piché, Montreal, Canada

[73] Assignee: Canadian Patents & Development Limited, Ottawa, Canada

[21] Appl. No.: 881,972

[22] Filed: Jul. 3, 1986

Related U.S. Application Data

[63] Continuation-in-part of Ser. No. 713,341, Mar. 18, 1985, abandoned.

[51] Int. Cl.$^4$ .............................................. G01N 9/00
[52] U.S. Cl. ...................................................... 73/32 A
[58] Field of Search ...................... 73/32 A, 596, 597; 310/336

[56] References Cited

U.S. PATENT DOCUMENTS

| | | | |
|---|---|---|---|
| 2,966,057 | 12/1960 | Heller | 73/599 |
| 3,400,363 | 9/1968 | Silverman | 73/596 |
| 3,995,501 | 12/1976 | Wiley | 73/597 |
| 4,297,608 | 10/1981 | Jensen | 73/32 A |
| 4,522,068 | 6/1985 | Smith | 73/597 |

OTHER PUBLICATIONS

Krautkramer, *Ultrasonic Testing of Materials*, 1983, pp. 581-582, Springer-Verlag, Berlin, Heidelberg, N.Y.
Corsaro, Acoustic Densitometer with Results for Polyethylene Oxide, 1974, Journal of Applied Physics, vol. 45, No. 1.

*Primary Examiner*—Stewart J. Levy
*Assistant Examiner*—Robert R. Raevis
*Attorney, Agent, or Firm*—Ronald G. Bitner

[57] ABSTRACT

The density of polyethylene is determined by measuring the velocity of ultrasound through the material. The determination of density is based on the correlation between the velocity of ultrasound in semi-crystalline materials and their density, and involves the measurement of time delays of a transmitted ultrasonic pulse from each of the front surface of the material the rear surface of the material and a reflector which are immersed in a liquid. Operating within a selected frequency range provides measurements of density while eliminating viscoelastic effects.

6 Claims, 5 Drawing Figures

ULTRASONIC DENSITY MEASUREMENT

This is a continuation-in-part application of co-pending application Ser. No. 713,341 filed Mar. 18, 1985, now abandoned.

BACKGROUND OF THE INVENTION

This invention relates to a method and apparatus for determining the density of polyethylene.

Polyethylene can be considered to be a binary mixture of an amorphous and a crystal phase. The degree of crystallinity affects the elastic properties such as elastic modulus, the impact strength and the melting point.

It is known that the density of polyethylene is directly related to the degree of crystallinity and thus the properties of the material. Density is the major criteria for characterizing and classifying polyethylene.

The most commonly used and accepted method for the determination of density is that of the "Density Gradient Column" defined by ASTM D1505 standard. A small piece of the sample is placed in a column of liquid which exhibits a known density gradient. After it has sunk to its equilibrium, the density is obtained by reading its position in the column. The technique and procedure are quite involved and suffer from numerous drawbacks. First the column must be prepared from a mixture of different solutions of known densities which are carefully added on top of one another. This is time consuming and requires skill to perform. The column which must be isolated from shock and vibrations in a constant temperature environment must then be calibrated using standard glass floats. The column having a limited lifetime (2 or 3 weeks) requires the calibration to be verified periodically. The material (powder, granules or pellets) for which the density is to be measured is press molded into plates roughly $15 \times 10 \times 0.2$ cm according to standardized procedures. The actual measurement is done on small pieces (typically $0.3 \times 0.3 \times 0.2$ cm) which are cut out of the plate. The mere action of cutting causes local impression and the pieces being small, their density will be affected. It is often the practice to allow these strains to relax by thermal conditioning. This again takes time. The pieces having been wetted down are gently introduced in the liquid where they settle in roughly 20 minutes. When a certain number of measurements have been made the column must be cleared of the material which is retrieved with a basket taking care not to upset the gradient.

It is generally known that the velocity of sound is related to the density of materials as well as other properties. For example, U.S. Pat. No. 4,327,587 discloses a method and apparatus for the continuous measurement of changes of rheological properties of monomer during polymerization by monitoring the propagation of ultrasonic oscillations. U.S. Pat. No. 4,297,608 discloses measuring equipment for acoustic determination of the specific gravity of liquids.

The velocity (v) at which sound propagates a material is related to the elastic modulus (M) and the density ($\rho$) as follows: $v = (M/\rho)^{\frac{1}{2}}$. In many usual cases, materials which show large variations of density ($\rho$), exhibit comparatively smaller changes of modulus, such that the velocity (v) decreases with increasing density. As an example, Aluminum, Iron, and Silver have densities $\rho_{Al} = 2.71$, $\rho_{Iron} = 7.8$ and $\rho_{Silver} = 10.5$ g/cm³ respectively; with corresponding velocities: $v_{Al} = 6.35$, $v_{Iron} = 4.5$ and $v_{Silver} = 3.6$ km/sec. However, this behaviour is not a general rule, and the velocity may appear independent of $\rho$, such as comparing Aluminum and Magnesium having densities $\rho_{Al} = 2.71$ and $\rho_{Mag} = 1.74$ g/cm³ and velocities $v_{Al} = 6.35$ and $v_{Mag} = 6.31$ km/sec. In other cases, the velocity will increase, or decrease even though the densities do not change much: Silver and Molybdenum where $\rho_{Silver} = 10.5$ and $\rho_{Moly} = 10.3$ g/cm³ while $v_{Silver} = 3.6$ and $v_{Moly} = 6.29$ km/sec. Finally the velocity may increase with increasing density such as in going from the Brass to Molybdenum for which $\rho_{Brass} = 8.56$ and $\rho_{Moly} = 10.3$ g/cm³ and $v_{Brass} = 4.28$ and $v_{Moly} = 6.29$ km/sec. These examples and many others show that the behaviour for the velocity of sound cannot a priori be predicted from the value of density.

For most solids, the elastic modulus, and thus the velocity does not vary with frequency. Materials for which the elastic modulus is independent of frequency are qualified as being purely elastic materials.

However, there exist other materials, such as polymers, of which polyethylene is an example, which are partly elastic and partly viscous. For such materials which are referred to as visoelastic materials, the velocity is not independent of frequency; at low frequency, the material appears more viscous than at high frequency where it appears elastic. At low frequency, the velocity increases with frequency.

SUMMARY OF THE INVENTION

It has been found that a high correlation exists between the velocity of ultrasound in polyethylene and the density thereof, and that this can be utilized to provide rapid determination of the density of polyethylene.

It has been found that in the frequency range up to 1 MHz polyethylene behaves as a viscoelastic material while above 1 MHz it behaves as an elastic material. The material, polyethylene is such that for a type of given density, the viscosity may have very different values. Velocity measurements taken at frequencies in the KHz range will vary not only with density but also by changes in the viscosity of the material.

It has further been found that when using frequencies greater than 1 MHz for the transmitted pulse, viscoelastic effects are eliminated and that density can be determined with insensitivity to changes in viscoelastic properties, such as viscosity. It was further found that above 1 MHz the measured velocity is independent of the frequency used.

The present invention provides a method and apparatus for determining the density of a polyethylene sample and involves immersing a transducer, a reflector, and the sample for which the density is to be determined in a liquid, transmitting an ultrasonic pulse at a frequency greater than 1 MHz to the sample and the reflector, measuring the time delays of a transmitted pulse reflected from each of the reflector, the front surface of the material, and the rear surface of the sample, computing the velocity of ultrasound through the material in accordance with the equation $v = c(\Delta t/2\tau + 1)$ wherein c is the velocity of ultrasound in the liquid, $\Delta t$ is the difference in the time delay taken with and without the sample in the liquid, $2\tau$ is the time delay of the reflected pulse returning from the rear surface of the sample after the front surface, and determining the density from a predetermined relationship of density to the velocity of ultrasound in the material.

DESCRIPTION OF THE PREFERRED EMBODIMENT

Figure 1:
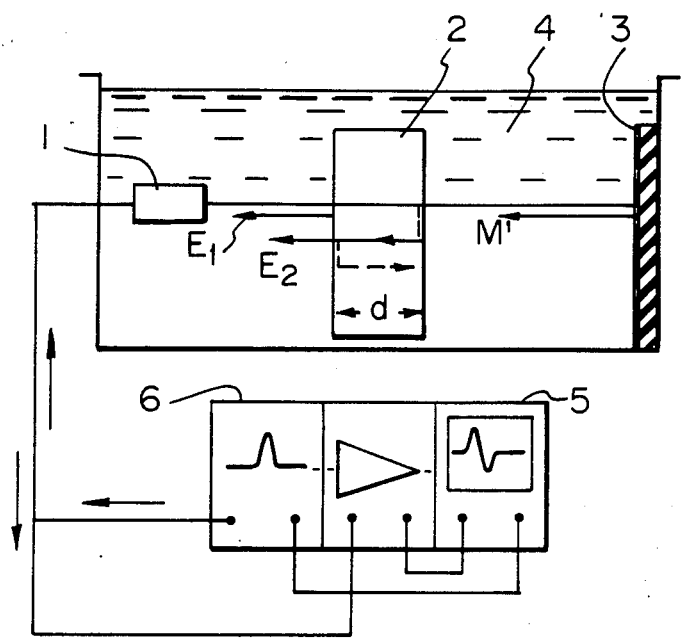
FIG. 1 is a schematic illustration of the system in accordance with the present invention.

With reference to FIG. 1, the present invention comprises a transducer 1 for transmitting an ultrasonic pulse through a sample 2 which is reflected back by the acoustic reflector 3. The above are immersed in liquid 4. Measuring means 5, shown as an oscilloscope, determines the delay time of a pulse emitted from the transducer 1 by means of a suitable pulser 6 and reflected back to the transducer 1.

Figure 2:
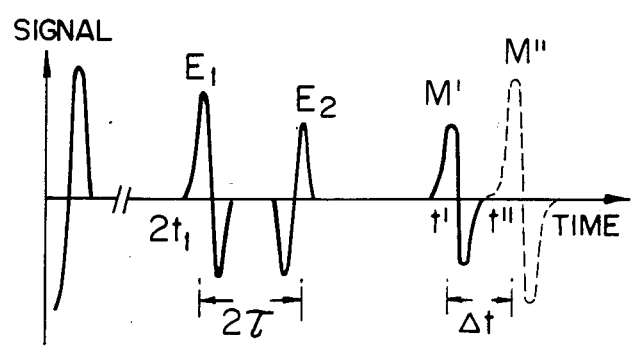
FIG. 2 is a graphic illustration showing the transmitted and reflected signal plotted against time.

FIG. 2 shows the various reflected signals utilized for determining the ultrasonic velocity through the sample.

With reference to FIGS. 1 and 2, an ultrasonic pulse preferably having a frequency greater than 1 MHz, and preferably from 2 to 10 MHz, is transmitted by the transducer 1. Part of the energy is reflected back ($E_1$) and returned to the transducer where it arrived at time $2t_1$ ($t_1$ being the time for the ultrasound to travel the liquid path one way). Part of the energy goes through the sample where it meets the second interface at time $t_1 + \tau$: again part of the energy is reflected, part is transmitted and so on. This gives rise to the formation of echos ($E_2$, etc...) which are observed at times $2t_1 + 2\tau$, $2t_1 + 4\tau$ .... Thus, if v is the velocity of ultrasound in the sample, then $$\tau = d/v$$

where d is the thickness of the sample. Part of the energy after having traversed the sample is transmitted forward in the liquid. This signal is reflected back to the transducer by the acoustic reflector 3. If $t_2$ is the time of flight from the sample to the mirror, the pulse will be observed at time $$t' = 2t_1 + 2\tau + 2t_2 = 2t_1 + 2d/v + 2t_2$$

If the sample is removed, the signal coming from the mirror arrives at time $$t'' = 2t_1 + 2d/c + 2t_2$$

where c is the velocity of ultrasound in the liquid. Considering the difference in the times of flight ($\Delta t = t'' - t'$) together with the expression for $\tau$ yields $$v = c(\Delta t/2\tau + 1).$$

The velocity of ultrasound in the liquid (c) can be found so that the velocity of ultrasound in the sample (v) is obtained from the sole measurements of time delays. It would be possible to perform such a measurement by replacing the reflector by a second transducer which would act as a receiver. The preferred embodiment where a sole transducer is used has the following advantages: (a) ease in mechanical adjustment and alignment, (b) a digital signal acquisition can be made with no error on the (zero) time reference, (c) the factor 2 in the equation $v = c(\Delta/2\pi + 1)$ reduces the error on the velocity by an equal factor of 2. This makes possible the rapid and fully automatic determination of velocity.

Experiments were conducted to establish the relationship of the velocity of ultrasound in polyethylene and density, as follows:

EXPERIMENTAL PROCEDURE AND RESULTS

The tests included 35 samples which cover a wide variety of commercial grade polyethylene. Most of the resins were furnished either by DuPont Canada or Union Carbide Limited and included low density, high density, linear low density and ultra high moclecular weight polyethylene (LDPE, HDPE, LLDPE and UHMWPE) with densities ($\rho$) ranging from 0.915 to 0.965 g/cm$^3$. The actual samples used in the measurements are the same as the press molded plates (approximately 80×50×1.9 mm) which are normally prepared for the density assessment. Measurement of density was also made in a density gradient column in the standard manner. To be able to define the standard deviation, values of density were obtained in different columns. The resulting density was found to be ±0.0006 g/cm$^3$.

The liquid used as demineralized water at 23° C. The transducer is of the commercially available immersion type. In order for the echos to be separated in time, the pulses must be short which requires a highly damped transducer operating at high frequency. However the attenuation of ultrasound in polyethylene increases rapidly with frequency and this sets an upper limit. The acoustic reflector located approximately 15 cm from the transducer was a flat piece of glass with an absorbent backing so that no signals (echoes) are issued other than the reflection from the front surface.

The electronics included a pulser capable of delivering short (100 n. sec) high voltage (300 volts) pulses with a repetition rate of 50 to 100 Hz. to excite the transducer. The echo signals were received by an amplifier having a 60 dB gain factor and a 20 MHz bandwidth. For these experiments the RF signal was monitored on an oscilloscope (Hewlett Packard Mod. 1743A) which is equipped with a dual time base that allows time delay measurements with adequate resolution (3 n.sec or better).

The ultrasound velocity in the water was measured by displacing the reflector by a known distance and noting the arrival time and found to be $(1.483 \pm 0.001) \times 10^5$ cm/sec. at 23° C.

Figure 4:
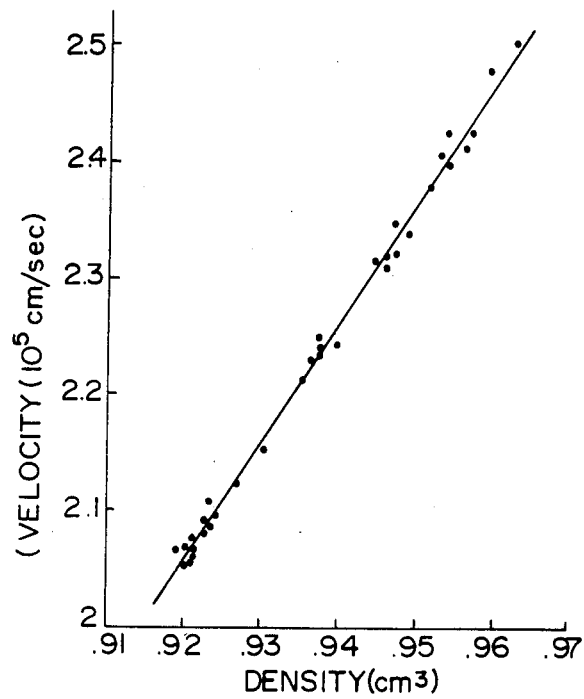
FIG. 4 is a graph showing results obtained for the measurement of ultrasound velocity in polyethylene as a function of density.

FIG. 4 shows the results obtained for the measurement of ultrasound velocity in polyethylene as a function of its density. The results were obtained using a 3 MHz transducer having a diameter of 1.25 cm. Observations showed variations in the range 1 to 30 MHz, showed that, within 1%, the velocity did not depend on the frequency at which the measurments were made.

Observations using transducers of increasingly larger diameter of from 0.2 cm to 4 cm showed decreasing scatter of results with larger diameters. It is believed the scatter is due to inhomogeneities across the sample and that increasing the diameter effectively provides a value averaged over a wider area. At 3 MHz it was found that a transducer having a beam width of 1 cm provided the desired averaging effect.

With reference to FIG. 4 a regression analysis was performed on the 35 data points. Using a linear model $v=ap+b$, the values for the coefficients and their standard error are: $a=(10.32\pm0.12)$ $10^5$ cm$^4$/g.sec and $b=-(7.43\pm0.12)$ $10^5$ cm/sec. The correlation factor is $r=0.998$, the standard error is $0.0102\times10^5$ cm/sec or, expressed in terms of a relative average value, $(\delta v/v)$ fit$=\pm0.0045$. This value is of the same order of magnitude as what was expected but even though the difference is small, $(\delta v/v)$ fit is larger than $(\delta v/v)$ expected. This discrepancy may be due to small amounts of additives in the samples. The ultrasound velocity can be considered as a measure of the fundamental elastic properties of the material whereas the standard density column method measures the apparent density. The presence of additives will not necessarily affect both quantities in the same fashion. Thus for the practical purpose of characterizing industrial materials the value of $(\delta v/v)$ fit can be considered as realistic since it integrates errors from all sources.

The results as shown in FIG. 4 indicate the relationship of density with respect to the velocity (v) of ultrasound in the sample as $0.0965\times10^{-5}$ v$+0.7218$. These results are for density in the range of 0.92 to 0.97 at a temperature of 23° C. It will be understood that other materials, or materials measured under different test conditions will have a different relationship of density to the measured ultrasound velocity.

Figure 5:
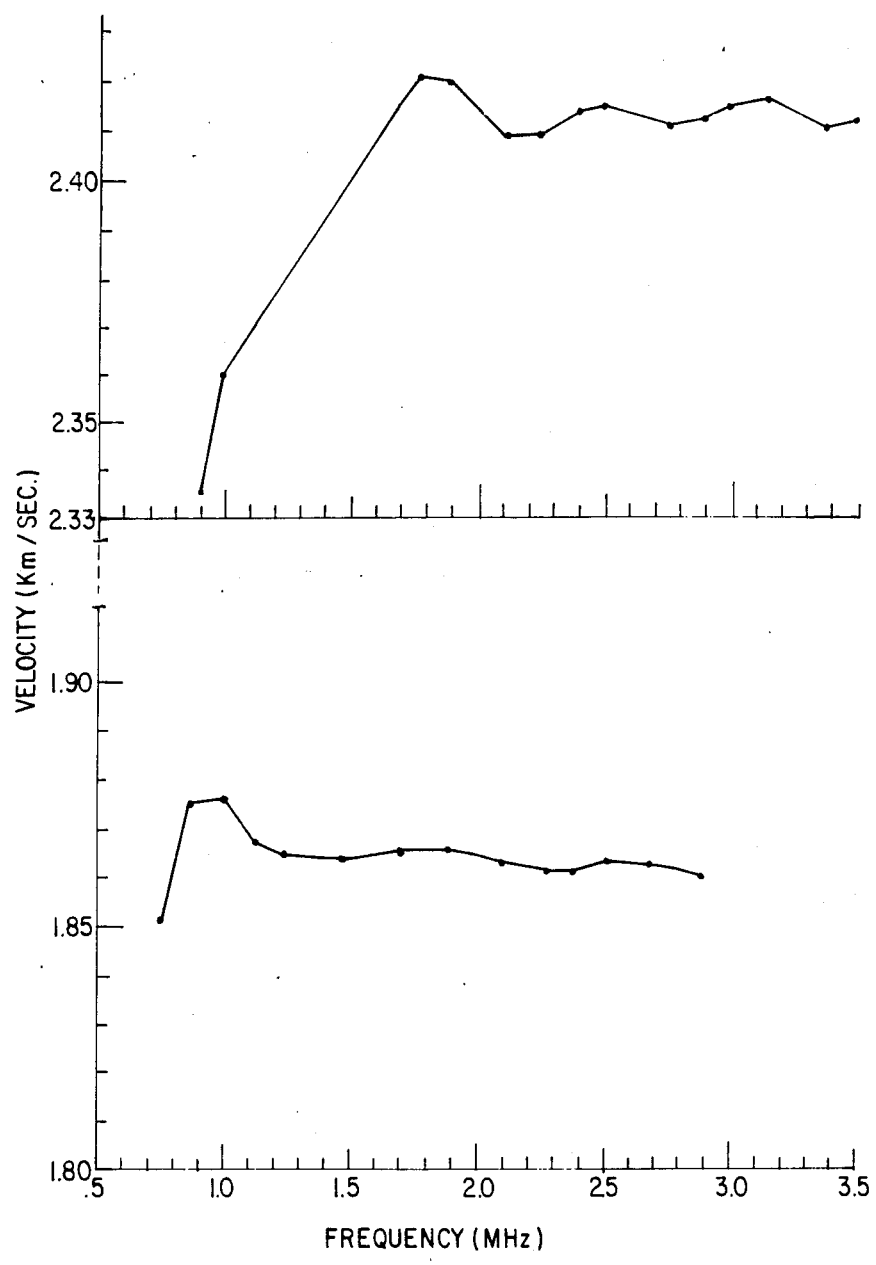
FIG. 5 is a graph showing velocity versus frequency for high and low density polyethylene.

FIG. 5 shows the effect of measurement frequency on the results for a high and low density polyethylene. It can be seen that above 1 MHz, the measured velocity is independent of frequency, within the experimental error of about 1%. However, at 1 MHz or less, the measured velocity varies with the frequency and therefore it is ot practical for the purpose of the present invention. It is believed that this difference is due to viscoelastic effects of the material. At the higher frequency the material appears as an elastic solid while at the lower frequency the material appears soft and viscous-like.

The use of frequencies above 1 MHz, so as to eliminate viscoelastic effects, allows making measurements of density while being insensitive to changes in the viscosity of the material. Below 1 MHz, velocity measurements of polyethylene are influenced by changes in the viscosity as well as the density of the material.

At higher frequencies, the ultrasonic pulse becomes progressively more attenuated. The preferred frequency range is from 2 to 10 MHz.

Figure 3:
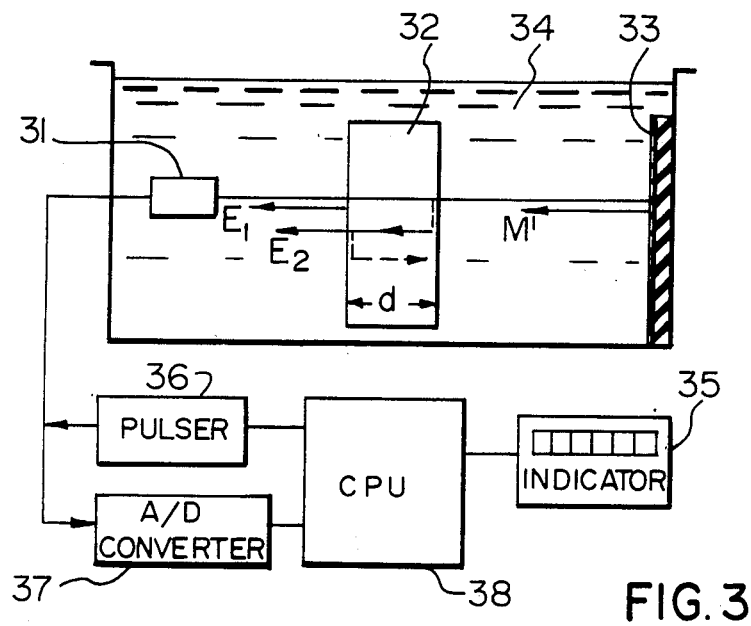
FIG. 3 is a schematic illustration of an alternate embodiment of the invention.

FIG. 3 shows an alternate embodiment wherein the density determination is performed digitally. In this embodiment the detected RF signal from transducer 31 is converted to digital form by an analog/digital converter 37. Preferably, the data is then submitted to a fast Fourier transform procedure, and then autocorrelated. The autocorrelated function shows a series of maximum values, or peaks, the position of which correspond to the different time delays are of interest. The experimentally determined relationship of ultrasonic velocity and density is entered into the CPU which then processes the time delays to provide a direct output of density.

I claim:

1. An apparatus for determining the density of a polyethylene sample comprising:

transducer means for transmitting and detecting an ultrasonic pulse having a frequency of greater than 1 MHz, an ultrasonic reflector, and means providing for immersion of the transducer means, reflector and the sample in a liquid;

means for measuring the time delays of a transmitted pulse reflected from each of the reflector, the front surface of the sample, and the rear surface of the sample; and means for computing the velocity of ultrasound through the sample in accordance with the equation $v=c(\Delta t/2\tau+1)$ wherein c is the velocity of ultrasound in the liquid, $\Delta t$ is the difference in the time delay taken with and without the sample in the liquid, $2\tau$ is the time delay of the reflected pulse returning from the rear surface of the sample after the front surface, wherein the density is determined from a predetermined relationship of density to ultrasonic velocity.

2. The apparatus of claim 1 wherein the transducer means provides an ultrasonic pulse having a frequency from 2 to 10 MHz.

3. The apparatus of claim 1 wherein the transmitted pulse has a beam width of from 1 to 2 cm.

4. The apparatus of claim 1, including means for computing the density of the sample from the computed velocity of ultrasound in accordance with the predetermined relationship of density to ultrasonic velocity.

5. A method for determining the density of a polyethylene sample comprising:

immersing a transducer, a reflector, and a sample for which the density is to be determined, into a liquid;

transmitting an ultrasonic pulse having a frequency of not less than 1 MHz to the sample and the reflector;

measuring the time delays of a transmitted pulse reflected from each of the reflector, the front surface of the sample, and the rear surface of the sample;

computing the velocity of ultrasound through the sample in accordance with the equation $v=c(\Delta t/2\tau+1)$ wherein c is the velocity of ultrasound in the liquid, $\Delta t$ is the difference in the time delay taken with and without the sample in the liquid, $2\tau$ is the time delay of the reflected pulse returning from the rear surface of the sample after the front surface; and determining the density from a predetermined relationship of density to the velocity of ultrasound in the sample.

6. The method of claim 5 wherein the ultrasonic pulse has a frequency of from 2 to 10 MHz.

* * * * *